(12) United States Patent
Csenar et al.

(10) Patent No.: US 10,744,263 B2
(45) Date of Patent: Aug. 18, 2020

(54) INJECTION DEVICE, IN PARTICULAR AN AUTO-INJECTOR

(71) Applicant: Pharma Consult Ges.m.b.H., Vienna (AT)

(72) Inventors: Markus Csenar, Vienna (AT); Andreas Schwirtz, Vienna (AT)

(73) Assignee: Pharma Consult Ges.m.b.H., Vienna (AT)

( * ) Notice: Subject to any disclaimer, the term of this patent is extended or adjusted under 35 U.S.C. 154(b) by 271 days.

(21) Appl. No.: 15/762,832

(22) PCT Filed: Sep. 22, 2016

(86) PCT No.: PCT/EP2016/072585
§ 371 (c)(1),
(2) Date: May 30, 2018

(87) PCT Pub. No.: WO2017/050919
PCT Pub. Date: Mar. 30, 2017

(65) Prior Publication Data
US 2018/0296760 A1    Oct. 18, 2018

(30) Foreign Application Priority Data

Sep. 24, 2015   (AT) .................... 50814/2015

(51) Int. Cl.
*A61M 5/20*      (2006.01)
*A61M 5/28*      (2006.01)
(Continued)

(52) U.S. Cl.
CPC .......... *A61M 5/2033* (2013.01); *A61M 5/281* (2013.01); *A61M 5/3202* (2013.01);
(Continued)

(58) Field of Classification Search
CPC ........ A61M 5/2033; A61M 2005/2073; A61M 5/3269; A61M 2205/58; A61M 5/326
See application file for complete search history.

(56) References Cited

U.S. PATENT DOCUMENTS

| 4,031,893 A | 6/1977 | Kaplan et al. |
| 5,295,965 A | 3/1994 | Wilmot |

(Continued)

FOREIGN PATENT DOCUMENTS

| DE | 10 2007 013836 A1 | 9/2008 |
| EP | 0 956 058 B1 | 1/2003 |

(Continued)

OTHER PUBLICATIONS

International Search Report of PCT/EP2016/072585, dated Dec. 14, 2016.

*Primary Examiner* — Nathan R Price
*Assistant Examiner* — Anna E Goldberg-Richmeier
(74) *Attorney, Agent, or Firm* — Collard & Roe, P.C.

(57) ABSTRACT

An auto-injector includes a base housing, an ampule, a needle arrangement, at least one drive assembly and a securing assembly which secures the drive assembly in its position with respect to the base housing until activated for the injection procedure. The securing assembly includes a securing cap with a cap jacket, a cap wall and a securing pin arranged inside the cap jacket. Arranged between the securing cap and the base housing is a guide arrangement with a first and a second guide element which define an adjustment path delimited in the axial direction on the side directed away from the distal end. In its release position, the securing cap is still arranged and held on the base housing.

33 Claims, 4 Drawing Sheets

Figure 1:
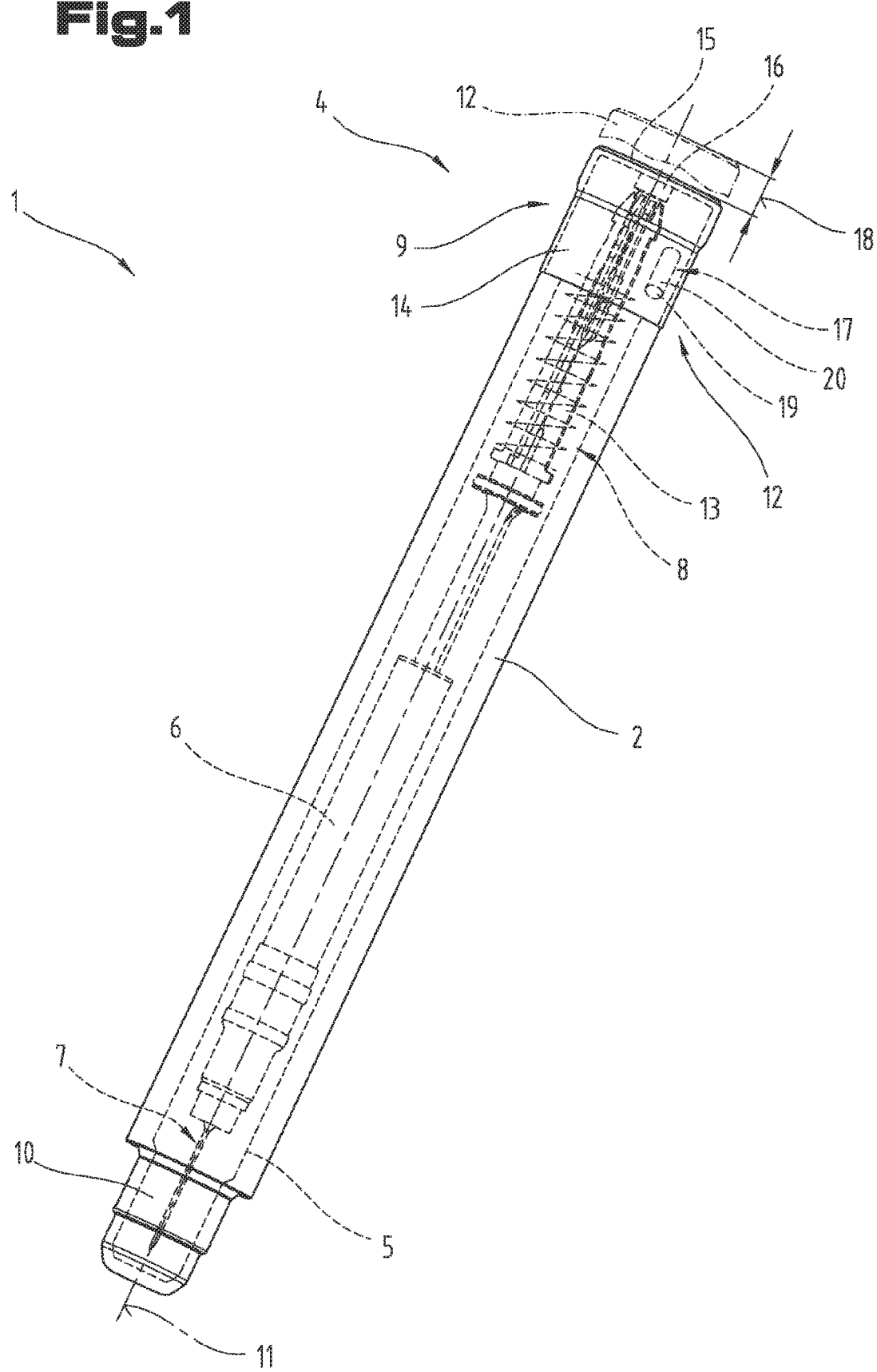

(51) Int. Cl.
 *A61M 5/32* (2006.01)
 *A61M 5/31* (2006.01)

(52) U.S. Cl.
 CPC ............ *A61M 2005/2073* (2013.01); *A61M 2005/3125* (2013.01); *A61M 2205/27* (2013.01)

(56) References Cited

U.S. PATENT DOCUMENTS

| | | |
|---|---|---|
| 5,354,286 A | 10/1994 | Mesa et al. |
| 5,658,259 A | 8/1997 | Pearson et al. |
| 6,767,336 B1 | 7/2004 | Kaplan |
| 9,265,891 B2* | 2/2016 | MacDonald ........ A61M 5/3155 |
| 9,421,336 B2 | 8/2016 | Ekman et al. |
| 9,872,961 B2 | 1/2018 | Fourt et al. |
| 9,956,353 B2* | 5/2018 | Rao .................... A61M 5/2033 |
| 2013/0190693 A1 | 7/2013 | Ekman et al. |
| 2013/0338593 A1 | 12/2013 | Wozencroft |
| 2018/0185582 A1* | 7/2018 | Mikkelsen .......... A61M 5/2033 |

FOREIGN PATENT DOCUMENTS

| | | |
|---|---|---|
| WO | 2005/113039 A1 | 12/2005 |
| WO | 2008/113198 A1 | 9/2008 |
| WO | 2011/101378 A1 | 8/2011 |
| WO | 2012/085589 A1 | 6/2012 |
| WO | 2014/062488 A1 | 4/2014 |
| WO | 2017/009284 A1 | 1/2017 |
| WO | 2017/009884 A1 | 1/2017 |

\* cited by examiner

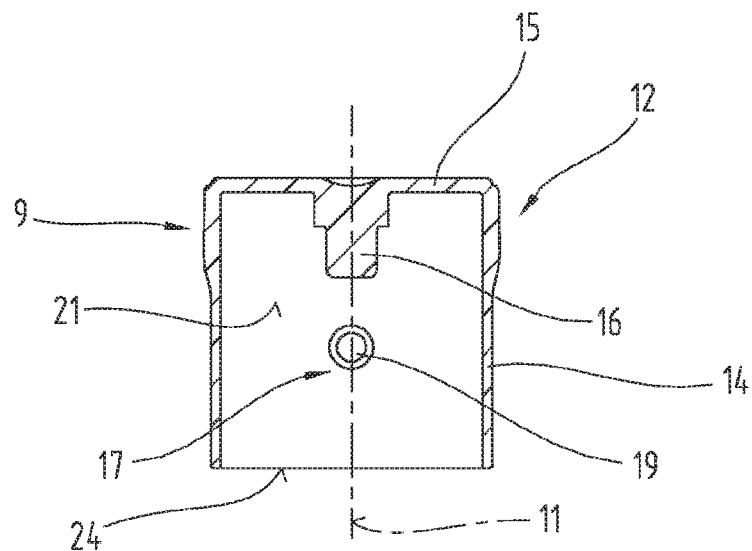
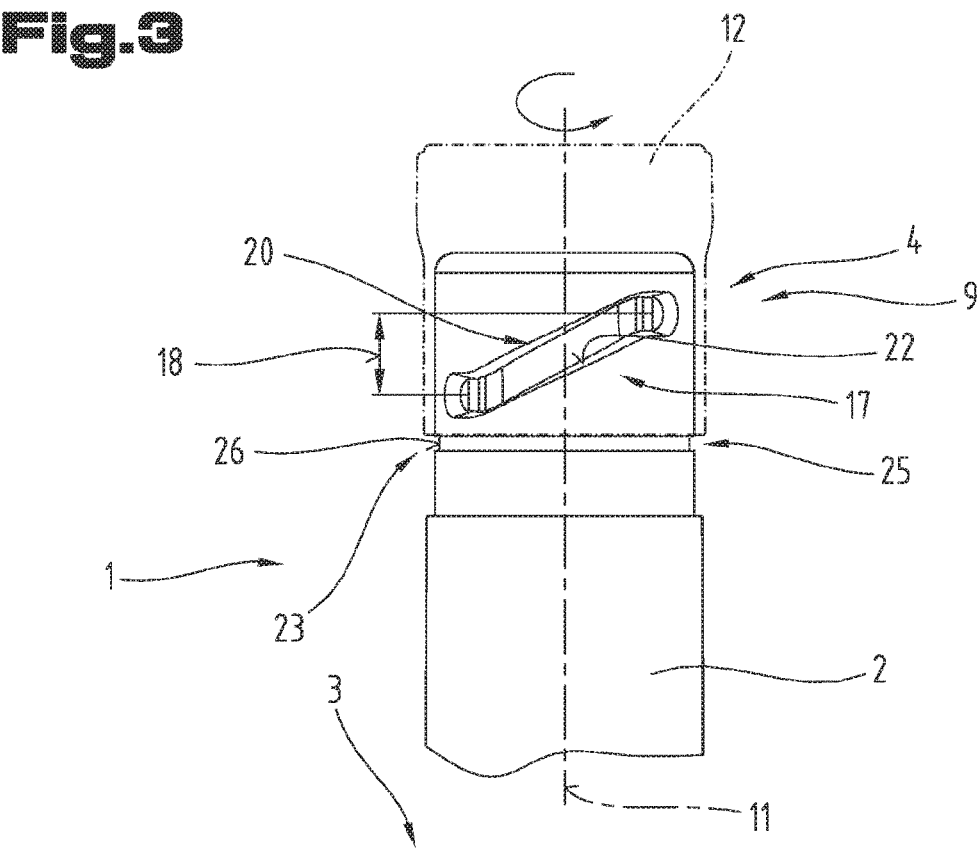

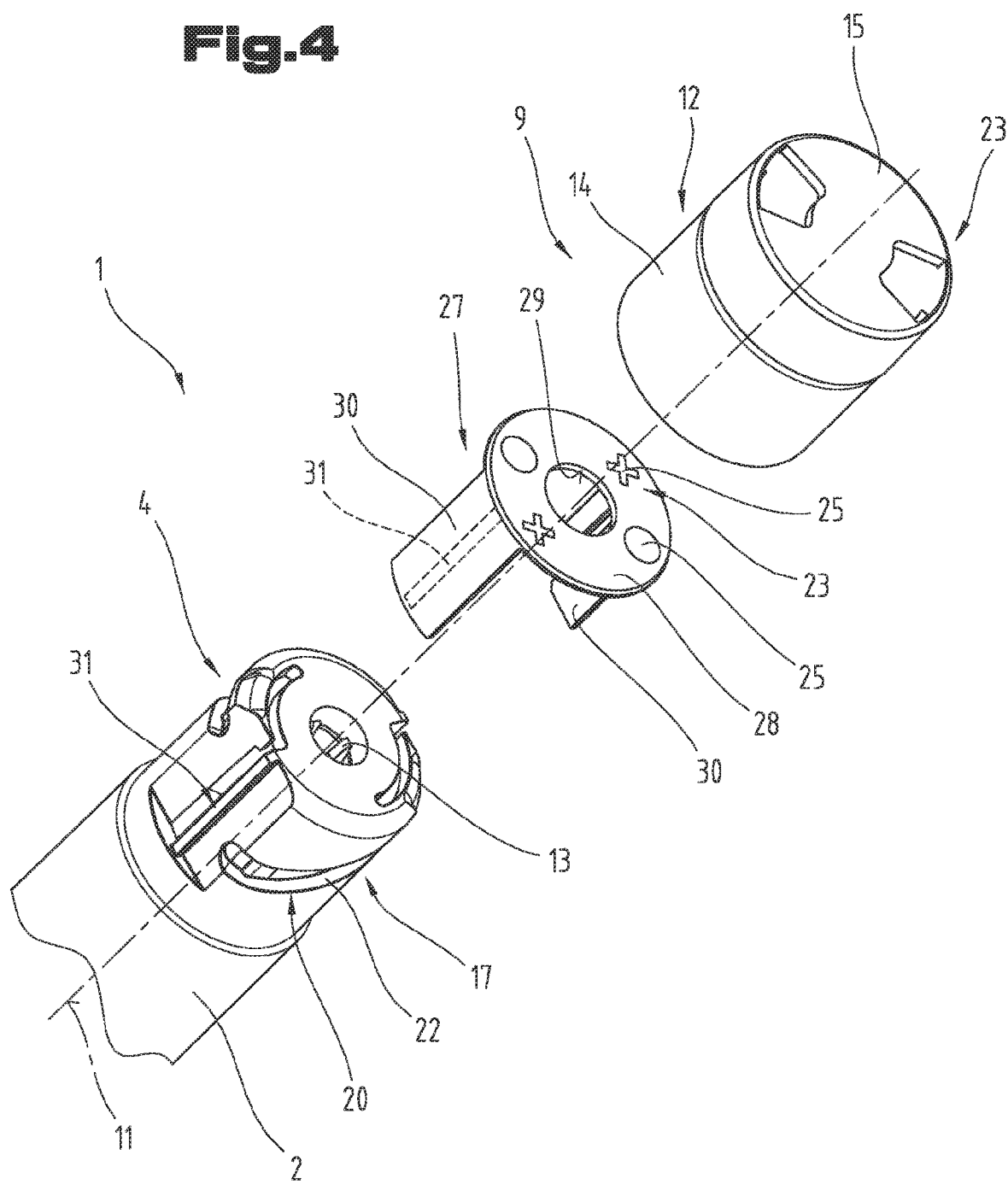

INJECTION DEVICE, IN PARTICULAR AN AUTO-INJECTOR

CROSS REFERENCE TO RELATED APPLICATIONS

This application is the National Stage of PCT/EP2016/072585 filed on Sep. 22, 2016, which claims priority under 35 U.S.C. § 119 of Austrian Application No. A 50814/2015 filed on Sep. 24, 2015, the disclosures of which are incorporated by reference. The international application under PCT article 21(2) was not published in English.

The invention relates to an injection device, in particular an auto-injector for automating dispensing of an injection fluid.

WO 2017/009284 A discloses an injection device of the generic type having a securing assembly to prevent undesired activation and associated dispensing of the injection fluid to be dispensed. The injection device comprises a sleeve-shaped base housing, a carpule containing the injection fluid to be dispensed during the injection procedure, a needle arrangement and a drive assembly with a drive means for automatically dispensing the injection fluid to be dispensed during the injection procedure. The drive assembly is secured in its position relative to the base housing by the securing assembly until activated for the injection procedure. The securing assembly comprises a securing cap and at least one retaining arm, the securing cap comprising a cap jacket, a cap wall and a securing pin arranged at a center on the cap wall inside the cap jacket and extending in the direction of a longitudinal axis. Arranged between the securing cap and the base housing is a guide arrangement with at least one first guide element and at least one second guide element cooperating therewith. The securing cap is displaceable on the base housing from its securing position in the axial direction and towards the end directed away from the base housing into a releasing position. The axial adjustment path is limited by the first and second guide element. In the releasing position, the securing cap is still disposed and retained on the base housing, and the at least one retaining arm is also released by the securing pin for the triggering and activation of the drive assembly. Although removal of the securing cap from the base housing and misorientation during dispensing is prevented, the dispensing operation no longer involves the usual task of removing a cap-shaped component to which users have long been accustomed.

DE 10 2007 013 836 A1 describes another injection device of the generic type, in particular an auto-injector, with a controlled needle retraction system. The injection device is designed to be switchable from a storage position into an injection position and comprises a sleeve-shaped base housing which comprises a distal end which can be directed towards a patient and a proximal end remote therefrom and a longitudinal axis extends between the ends. The injection device further comprises a carpule containing an injection fluid to be dispensed during the injection procedure and a needle arrangement and a securing assembly. The needle arrangement is disposed in front of the carpule in the section of the distal end in the storage position of the injection device. The securing assembly is disposed in the region of the proximal end of the base housing and holds the drive assembly in position relative to the base housing until activated for the injection procedure. The securing assembly comprises a securing cap with a cap jacket, a cap wall and a securing pin arranged at a center on the cap wall inside the cap casing and extending in the direction of the longitudinal axis. In the storage position, the securing cap is retained on the base housing in a securing position for the at least one drive assembly and in the securing position, the securing pin holds at least one retaining arm of the securing assembly in a stationary position in the radial direction relative to the longitudinal axis. The retaining arm constitutes a connecting member to the drive assembly. In order to release the drive assembly, the securing cap is also displaceable in the circumferential direction about the longitudinal axis from its securing position into a releasing position. To this end, a guide arrangement having a first guide element and a second guide element cooperating therewith is provided. In the releasing position, the securing cap is still arranged and held on the base housing and the retaining arm is also released by the securing pin for triggering and activating the drive assembly.

WO 2012/085589 A1 describes an auto-injector having a sleeve-shaped base housing in which an ampule containing the injection fluid to be dispensed during the injection procedure, a needle arrangement, a drive assembly and a securing assembly are disposed. The securing assembly secures the position of the drive assembly with respect to the base housing until activated for the injection procedure and comprises a securing cap with a cap jacket, a cap wall and a securing pin arranged on the cap wall inside the cap jacket and extending in the direction of the longitudinal axis. In the securing position, the securing pin pushes the retaining arms of the securing assembly outwards in the radial direction and therefore holds them in a stationary position relative to the longitudinal axis, and the retaining arms form connecting members to the drive assembly. The securing cap has to be moved from its securing position in the axial direction and towards the end directed away from the distal end into a releasing position and completely removed. The securing assembly further comprises an activation cap disposed inside the securing cap and retained on the base housing. At its center, the activation cap has an orifice for accommodating the securing pin of the securing cap. The central orifice in the activation cap is surrounded by a tubular shoulder which comes into contact with the latch arms when the trigger cap is moved axially in the direction towards the distal end and moves them inwards in the radial direction and in the direction towards the longitudinal axis and thus releases the latched position so that automated dispensing can proceed. In its initial position, the activation cap is held stationary in the proximal direction on the base housing relative thereto and only a displacement path in the distal direction is possible for effecting the triggering movement. The activation cap is reset from its triggering position to its initial position by means of resilient arms extending out from the activation cap in the axial direction in cooperation with inclined contact surfaces on the internal face of the base housing.

An injection device of the generic type, in particular an auto-injector, is also known from WO 2011/101378 A1 and US 2013/01900693 A1 running in parallel therewith. Amongst other things, this injection device also comprises a securing assembly for a drive assembly located in the region of a proximal end. The securing assembly comprises a securing sleeve which is pivotable exclusively in the circumferential direction about a longitudinal axis from a securing position into a releasing position. To this end, a guide arrangement with first guide elements and second guide elements cooperating therewith are provided. In the releasing position, the securing sleeve is still arranged and held on the base housing, and in the securing position the trigger button for activating the drive assembly is prevented from effecting an axial movement in the direction towards the distal end of the injection device by means of a projection located on an internal face of the securing sleeve. When the projection is moved away by a rotating movement of the securing sleeve, an elongate rib that was previously lying in contact with the projection can be released by means of the trigger button and the drive assembly activated for automatically dispensing the medicament.

Another injection device of the generic type, in particular an auto-injector, is described in U.S. Pat. No. 5,354,286 A1. The injection device is designed to be displaceable from a storage position into an injection position and comprises a sleeve-shaped base housing which comprises a distal end which can be directed towards a patient and a proximal end remote therefrom and a longitudinal axis extends between the ends. Its securing assembly is also disposed in the region of the proximal end of the base housing and holds the drive assembly in position relative to the base housing until activated for the injection procedure. The securing assembly comprises a securing cap with a cap jacket, a cap wall and a securing pin arranged on the cap wall inside the cap jacket and extending in the direction of the longitudinal axis. In the storage position, the securing cap is held on the base housing in a securing position for the at least one drive assembly. In the securing position, the securing pin holds a retaining arm of the securing assembly in a stationary position in the radial direction relative to the longitudinal axis. In order to release and activate the drive assembly, the securing cap together with the securing pin disposed in it must be pulled off the base housing in the axial direction towards the direction remote from the distal end and removed from the base housing. An orifice therefore remains visible in the region of the proximal end of the base housing.

An automated injection device for dispensing a medicament has become known from U.S. Pat. No. 6,767,336 B1 and comprises a support housing in which the drive assembly, the storage container for the medicament and the needle arrangement are disposed. An elastically deformable and pierceable protection element is fitted over the cannula of the needle arrangement which is connected to the needle holder. The needle holder firstly supports the needle and is connected to the storage container for the medicament at its distal end. The cannula therefore has a permanent flow connection to the interior and hence the medicament. In the region of the distal end, a needle guard element is mounted on the support housing so as to be longitudinally slidable and is provided with another drive means. Starting from the proximal end of the support housing, it is provided with a trigger sleeve and the latter occupies at least certain regions of the support housing. The first drive assembly is also provided with a cap-shaped securing element having a securing pin extending through the injection device in order to prevent undesired triggering. For unlocking purposes, the cap together with the securing pin has to be pulled completely off the support housing. The needle guard element and its drive means are triggered during the relative movement of the medicament container together with the needle arrangement disposed thereon. Both the trigger sleeve and the needle guard element are respectively disposed on the common support housing in a tightly adjoining arrangement and one after the other in the axial direction. The disadvantage of this is that after the securing cap has been pulled off, an orifice is visible both in the region of the distal end and in the region of the proximal end of the support housing.

U.S. Pat. No. 4,031,893 A describes another auto-injector of a similar design in which the activatable drive assembly and the medicament container with the needle arrangement disposed thereon are housed in a common support housing. The drive assembly is again secured against inadvertent triggering by means of a cap-shaped securing element having a securing pin extending through the injection device. At its external face, the support housing is surrounded by a sleeve-shaped component which is coupled with an additional trigger sleeve at its proximal end. Once the securing cap together with the securing pin has been completely removed, the trigger sleeve triggers the drive assembly, as a result of which the medicament container together with the needle arrangement is moved in the direction of the distal end. The cannula, which is in a permanent flow connection with the interior of the medicament container, is surrounded by an elastically deformable protective sheath which is supported on the internal face of the distal end of the support housing. During the forward movement, the cannula pierces the elastically deformable protective sheath and moves out of the support housing in readiness for the injection. On termination of the injection procedure, the elastically deformable needle protective sheath causes the needle arrangement together with the medicament container to be moved back into the interior of the support housing. Again, the disadvantage of this is that once the securing cap has been pulled off, an orifice is visible both in the region of the distal end and in the region of the proximal end of the support housing.

An automated injection device for dispensing a medicament has become known from U.S. Pat. No. 5,295,965 A in which the outer casing acts as a needle guard sleeve. It extends from the distal end directed towards the patient to close to the proximal end where it can be operated by means of a cap-shaped activation cover. For activation purposes, a securing pin disposed in the region of the proximal end which secures the first drive assembly until activation by means of the cap-shaped activation cover has to be released. After the securing pin has been removed, the cap-shaped activation cover can be moved relative to the support housing and the needle guard sleeve, as a result of which both the first drive assembly and the needle guard sleeve are activated. The needle guard sleeve is in turn provided with a separate spring device by means of which it is moved into the position covering the needle. Again, the disadvantage of this is that once the securing pin has been pulled off, an orifice is visible both in the region of the distal end and in the region of the proximal end of the support housing.

Another automated injection device for dispensing a medicament from an ampule has become known from U.S. Pat. No. 5,658,259 A or EP 0 956 058 B1. To this end, the ampule with the medicament is disposed inside a support housing and the latter is additionally provided with a first drive assembly for the operation thereof and dispensing of the medicament. Disposed inside the support housing is a needle guard sleeve which can be triggered by the longitudinal displacement of the needle holder which is also provided with a displacement element. To effect a release from the locked position, a cover cap firstly has to be removed from the region of the proximal end of the injection device, thereby enabling access to a securing pin. The securing pin must be pushed in the direction towards the distal end in order to operate the first drive assembly. The needle guard sleeve is retained inside the support body by means of a catch connection until activation by means of the displaced needle holder. After the medicament has been dispensed, the needle guard sleeve covers the end of the needle projecting out beyond the auto-injector. This injection device has a different activation assembly and operating mode because the injection device firstly has to be positioned on the desired injection point and only then is the first drive assembly activated by pushing in the securing pin. WO 2005/113039 A1 describes an auto-injector for dispensing a medicament based on a different design which comprises a stationary support housing having an inner and outer housing wall in the region of the distal end. Disposed in the support housing is the drive assembly, the storage container for the medicament and the needle arrangement. The proximal end of the needle is in a permanent flow connection with the interior of the storage container and hence with the medicament. The automatic injection device further comprises a needle guard element displaceable in the direction of the longitudinal axis which is mounted so as to be guided between the inner and outer housing wall of the support housing. This sleeve-shaped needle guard element is provided with an additional drive assembly in order to move it into the position covering the needle on release. In addition, a gripping means may be provided on the external face of the support housing to improve handling. Disposed at the end lying opposite the needle—namely the proximal end—is an actuation mechanism for actuating the first drive assembly. In this context, the actuation movement is a pushing movement in the direction perpendicular to the longitudinal axis. After the transverse movement and unlocking of the retaining device, the first drive assembly is activated, as a result of which the plunger is moved together with the storage container in the direction of the distal end until a stop of the storage container facing the proximal end moves into abutment with a stop of the inner housing wall of the support housing. Simultaneously with this longitudinal displacement, the needle guard element is also activated and is thus moved into contact with the dispensing site of the medicament. After the medicament has been dispensed and the entire injection device has been moved away, the needle guard element is moved further forwards until the needle is completely covered by means of the already activated drive mechanism.

The objective of this invention was to overcome the disadvantages of the prior art and propose an injection device by means of which a user is in a position to be able to dispense the medicament easily and safely and thus avoid an incorrect deployment direction and hence associated possible undesired needlestick injuries.

This objective is achieved by means of an injection device based on the claims.

The injection device proposed by the invention is designed to be displaceable from a storage position into an injection position and comprises

- a sleeve-shaped base housing, which base housing has a distal end which can be directed towards a patient and a proximal end remote therefrom, between which ends a longitudinal axis extends,
- an ampule containing an injection fluid to be dispensed during the injection procedure,
- a needle arrangement which is disposed in front of the ampule in the section of the distal end in the storage position of the injection device,
- at least one drive assembly, which drive assembly comprises a drive means for automatically dispensing the injection fluid to be dispensed during the injection procedure,
- a securing assembly, which securing assembly secures the at least one drive assembly in its position with respect to the base housing until activated for the injection procedure,
- the securing assembly comprising a securing cap and at least one retaining arm, and the securing cap comprising a cap jacket, a cap wall and a securing pin disposed inside the cap jacket at a center on the cap wall and extending in the direction of the longitudinal axis,
- and in the storage position, the securing cap is retained on the external face of the base housing in a securing position for the at least one drive assembly, and in the securing position, the securing pin is disposed inside the at least one retaining arm at the axial center of the securing assembly and holds the at least one retaining arm of the securing assembly in a stationary position in the radial direction relative to the longitudinal axis preventing a radial movement inwards in the direction towards the longitudinal axis, and the at least one retaining arm forms a connecting member to the drive assembly,
- a guide arrangement having at least one first guide element and at least one second guide element cooperating therewith is provided between the securing cap and the base housing, and
- the ampule, the needle arrangement, the at least one drive assembly and the securing assembly are accommodated or disposed in the base housing in at least certain regions, and the securing assembly and the drive assembly are disposed in that part of the base housing constituting the proximal end, and
- the at least one first guide element is formed by a projection which is disposed or arranged on an internal face of the cap jacket and projects out from the latter in the direction towards the longitudinal axis,
- and the at least one second guide element is formed by a guideway, in particular recessed in the base housing, which is arranged or disposed on the base housing in the region of the proximal end, or the at least one second guide element is formed by a preferably circumferentially extending groove-shaped recess and/or projection disposed or arranged in the region of the proximal end of the base housing,
- and the securing cap is displaceable from its securing position in the axial direction and towards the end remote from the distal end into its releasing position,
- and the at least one first guide element and the at least one second guide element define an adjustment path of the securing cap delimited in the axial direction between its securing position and its releasing position, as a result of which the securing cap is still disposed and retained on the base housing in its releasing position and the at least one retaining arm for triggering and activating the drive assembly is also released by the securing pin at the same time, and
- the securing assembly further comprises an overcap which is detachably retained on the securing cap.

The advantage achieved as a result is that a potential misorientation of the injection device after unlocking the securing assembly and the release for the injection procedure associated therewith can be prevented. The securing cap retained on the housing together with its securing pin extends through an orifice of the base housing and thus holds the retaining arms in position but, if it were removable, the securing cap would otherwise leave an open hole in the region of the rear wall of the base housing after having been removed. This could result in a situation where the user has not placed the intended distal end from which the cannula extends for the injection procedure facing the intended injection site but the incorrect proximal end from which the securing cap has been completely pulled off or removed. If, in this case, the thumb or another body part were still touching that end that is now opposite the intended injection site and from which the cannula will extend after activation, the injection would proceed and the associated dispensing of the injection fluid would take place in this body part and not at the intended injection site. However, since the securing cap in fact remains on the base housing even after the movement into the releasing position and can no longer be removed, any such misorientation can be ruled out. This potential misorientation occurs in particular in situations in which the user is experiencing heightened stress.

If the at least one first guide element is formed by a projection which is disposed or arranged on an internal face of the cap jacket and projects out from the latter in the direction towards the longitudinal axis, a reliable adjusting movement of the securing cap on the base housing can be obtained. This also avoids obstructive projections in the securing cap and a circumferentially closed design of the cap jacket.

If the at least one second guide element is formed by a guideway, in particular recessed in the base housing, which is arranged or disposed on the base housing in the region of the proximal end, opting for the guideway enables the longitudinal extension and hence adjusting movement of the securing cap to be set. Furthermore, however, a definite axial length of the adjustment path can be set. This also applies in the case where a pivoting or rotating movement of the securing cap relative to the base housing is selected. If, on the other hand, the at least one second guide element is formed by at least one preferably circumferentially extending groove-shaped recess and/or a projection disposed or arranged in the region of the proximal end of the base housing, a simple snap-fit connection can be obtained between the securing cap and the base housing in at least one of the positions, namely the securing position and/or the releasing position.

The fact that the securing assembly further comprises an overcap which is detachably retained on the securing cap offers the user or operator the possibility of being able to remove a cap-type component from the injection device after moving the securing cap into the releasing position whilst nevertheless leaving the securing cap still retained on the base housing.

Another possible embodiment comprises the features whereby the guideway has a different pitch with mutually different pitch angles in its longitudinal extension relative to a plane oriented in a direction perpendicular to the longitudinal axis. This enables the relative pivot or rotation angle of the securing cap relative to the base housing to be set depending on the selected pitch angle.

Based on another embodiment, the pitch angle of the guideway is flatter in the region of the securing position and/or the releasing position than in the intermediate section thereof extending between the securing position and the releasing position. This enables a better axial positioning of the securing cap on the base housing to be obtained in the securing position and/or the releasing position.

Another preferred embodiment is characterized by the fact that the securing assembly further comprises a display unit, which display unit displays at least one of the two positions of the securing cap relative to the base housing. This provides a simple way of indicating to the user by means of the display unit which position the injection device is in, in particular the securing assembly thereof.

It may also be of advantage if the display unit comprises at least a first display means which is arranged or disposed in the region of the securing cap. This offers an easy way of clearly displaying the securing cap and its relative position with respect to the base housing.

Another alternative embodiment is characterized by the fact that the at least one first display means is formed by an orifice and/or a cap rim of the cap jacket spaced at a distance apart from the cap wall. This offers the possibility of providing a clear display, even in the case of a rotating or pivoting movement in addition to the axial displacement, thereby enabling the operating mode of the injection device to be indicated.

Another possible and optionally alternative embodiment is based on features whereby the display unit comprises at least one second display means which is preferably arranged or disposed in the region of the base housing. This in turn provides an easy way of displaying the relative disposition and position of the securing cap in at least one relative position with respect to the base housing.

Based on another embodiment, the display unit further comprises a display mounting element, which display mounting element is disposed inside the cap jacket and directly adjacent to the cap wall, and the display mounting element is guided and displaceable on the base housing in the axial direction and the securing cap can also be pivoted relative to the display mounting element about the longitudinal axis, and the display mounting element is also held in position on the securing cap relative thereto in the direction of the longitudinal axis. This means that a clear display of the operating mode can always be provided, including in the region of the cap wall or end wall of the securing cap even when there is a pivoting or turning movement of the securing cap with respect to the base housing. In this context, the display mounting element can be moved exclusively in the axial direction with respect to and on the base housing but a pivoting or rotating movement of the securing cap can still be effected relative to both the display mounting element and the base housing.

Another embodiment is characterized by the fact that the display mounting element comprises a disk-shaped main body with an orifice disposed at its center and at least one guide web protruding in the axial direction therefrom. This offers a simple way of enabling the display mounting element to be accommodated inside the securing cap whilst nevertheless providing a reliable axial guiding action on the base housing.

Another preferred embodiment is characterized by the fact that the at least one guide web is disposed in the outer circumferential region of the disk-shaped main body. This enables a receiving means to be provided between the cap jacket and base housing whilst requiring a minimum amount of space.

It may also be of advantage if a longitudinal guide arrangement is arranged or disposed between the at least one guide web and the base housing. This enables the entire display mounting element to be guided on the base housing reliably and in a straight line in the axial direction.

Another embodiment is characterized by the fact that the display unit comprises at least one first display means formed by an orifice in the cap wall of the securing cap. This provides a simple optical visibility on the injection device.

Another possible embodiment comprises the features whereby the display unit comprises at least one second display means which is disposed on the display mounting element, in particular on the disk-shaped main body of the display mounting element. This offers the possibility of being able to change the display of the display means in an easy manner. This can be achieved by simply replacing the display mounting element, for example.

Based on another embodiment, the at least one second display means is selected from the group comprising a symbol, color coding, marking ring, image, embossed print, braille. This enables the desired selected visual display to be adapted to different application requirements.

Another preferred embodiment is characterized by the fact that mutually engaging catch means are provided between the overcap and the securing cap, in particular in the region of the cap jacket. This offers an easy way of being able to set the releasing force of the overcap from the securing cap.

Another possible embodiment is based on features whereby the overcap engages around the securing cap in the region of its cap jacket.

Finally, an alternative embodiment has features whereby the overcap completely accommodates the securing cap.

To provide a clearer understanding, the invention will be described in more detail with reference to the appended drawings.

Figure 5:
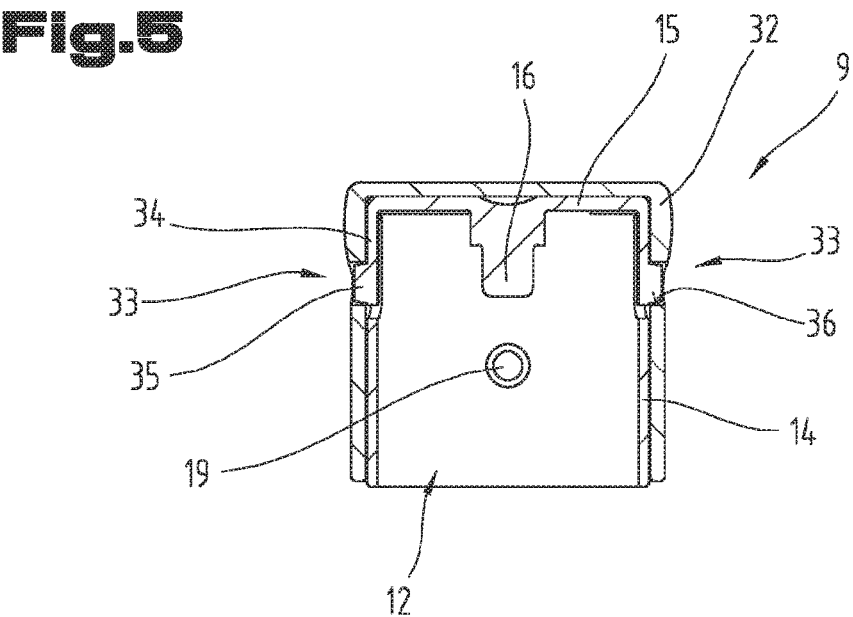
Figure 6:
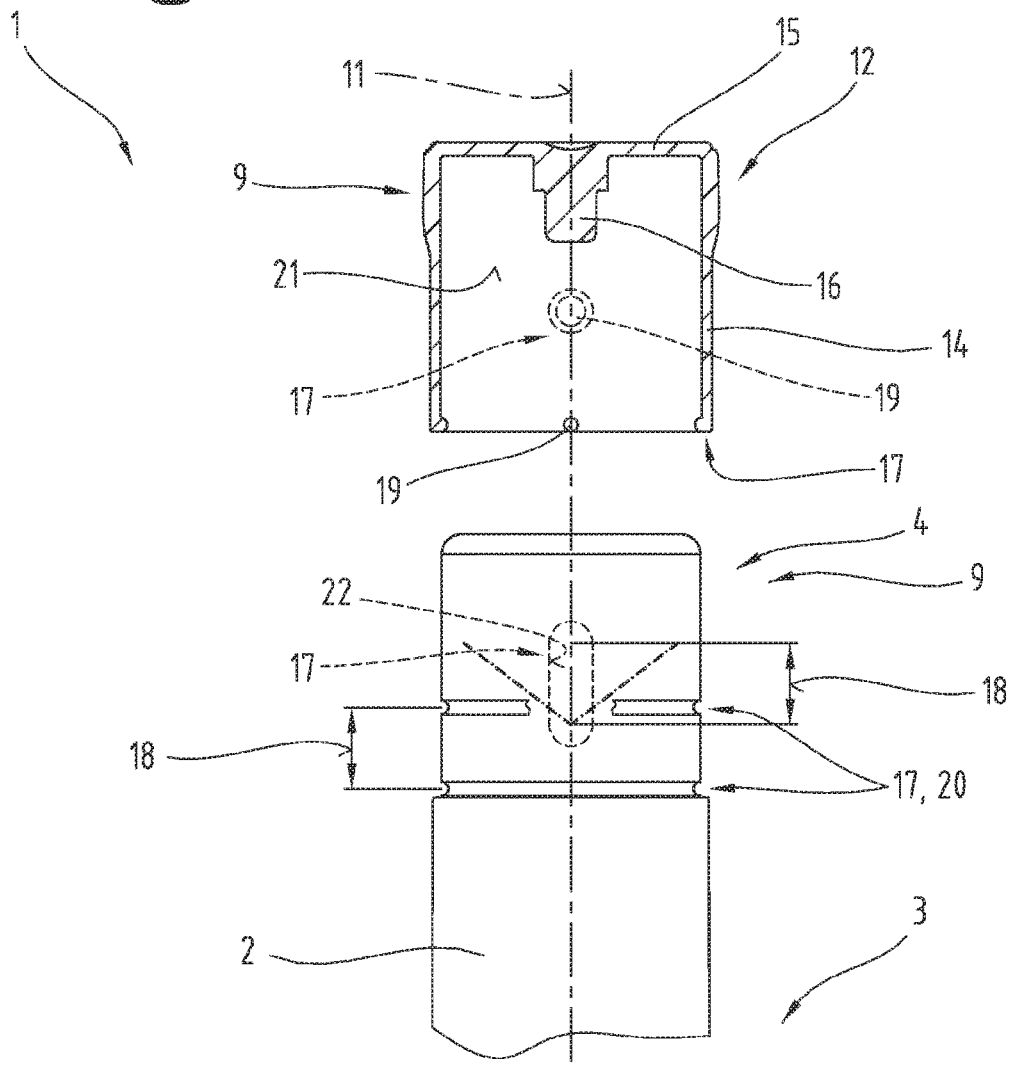

These are highly simplified, schematic diagrams illustrating the following:

FIG. 1 a diagrammatic illustration of one possible embodiment of an injection device in its storage position;

FIG. 2 one possible embodiment of a guide arrangement on a securing cap for the injection device, viewed in axial section;

FIG. 3 a view of one possible embodiment of a base housing in the region of its proximal end, for a securing cap based on FIG. 2;

FIG. 4 another possible embodiment of a securing assembly of an injection device, showing a perspective and exploded view of the components;

FIG. 5 another possible embodiment of the securing cap fitted with a removable overcap, viewed in axial section;

FIG. 6 other possible embodiments of the securing assembly seen in an exploded view of the components and in partial section.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described.

The expression "in particular" used hereafter should be construed as meaning that a possible, more special embodiment is being described or a more specific aspect of an object or method step, but not necessarily a preferred embodiment as such.

FIGS. 1 to 6 respectively illustrate an injection device 1 for dispensing a medicament or an injection fluid, the injection device 1 being of the automated dispensing type. Accordingly, it may be referred to by the standard technical term as an auto-injector. The individual embodiments in FIGS. 1 to 6 have only slight differences from one another but each of the embodiments may constitute an independent embodiment in its own right although individual design details from the different embodiments may also be combined with one another.

A whole range of different automated injection devices 1 are known and they are always designed to be automatically displaceable from a storage position into an injection position. This being the case, both the injection operation and the operation of dispensing the injection fluid to be dispensed or medicament take place automatically but only after release and deliberate activation on the part of the user.

To prevent infection or the transmission of diseases during the course of the injection operation and the associated dispensing operation, at least those components which penetrate the body during the injection operation are kept in a sterile state whilst in the storage position.

The injection device 1 generally comprises a plurality of individual components as well as assemblies made up of them. Accordingly, the injection device 1 may comprise a usually sleeve-shaped base housing 2 having a distal end 3 intended to face the patient and a proximal end 4 remote therefrom. Other terms which may be used to describe position are front and rear, in which case "front" refers to the distal end 3 and "rear" to the proximal end 4. Depending on the design of the injection device 1, the base housing 2 may also be described as a triggering sleeve or activation sleeve. This is the case with an embodiment whereby the injection device 1 is activated and hence the liquid medicament or injection fluid is dispensed in a known manner due to the relative movement of the base housing 2 with respect to the injection site.

As may be seen from the schematically simplified diagram of FIG. 1, a separate support housing 5 is at least partially accommodated or housed inside the base housing 2. The injection device 1 may also comprise another storage vessel such as an ampule 6, a needle arrangement 7, at least one drive assembly 8 and a securing assembly 9. The needle arrangement 7 comprises a cannula, one end of which is provided for piercing the body and the other end provides a flow connection to the injection fluid in the ampule 6 even before the injection procedure or does not establish a flow connection to the interior of the ampule 6 until the injection procedure is underway.

The housing vessel for the injection fluid is provided in the form of an ampule 6 in this instance, in which the medicament, injection fluid or active ingredient to be injected is already held in supply and ready for dispensing whilst in the storage position. Accordingly, it is possible for the ampule 6, the needle arrangement 7, the at least one drive assembly 8 as well as parts of the securing assembly 9 to be received on or disposed on at least certain regions in the base housing 2. If a separate support housing 5 is provided, the aforementioned components may also be received or disposed in it. The needle guard element 10 may be disposed between the support housing 5 and the base housing 2 as viewed in the radial direction.

The drive assembly 8 is actively connected to the ampule 6 to enable at least the dispensing of the medicament or injection fluid after piercing. In order to prevent undesired needlestick injuries after dispensing and before the injection device 1 has been removed from the body, the latter may also have a needle guard element 10 which reliably covers at least the used cannula portion. To this end, another activatable drive unit may be provided, although this is not illustrated with a view to retaining greater clarity. However, it is not absolutely necessary to provide the needle guard element 10 together with the other drive unit.

Extending between the distal end 3 and the proximal end 4 of the base housing 2 is a longitudinal axis 11. However, the longitudinal axis 11 may also be regarded as a common axis for the injection device 1 as a whole.

The needle arrangement 7 is usually disposed in front of the ampule 6 in the storage position and is located in the front region and hence in the region of the distal end 3.

The drive assembly 8 comprises at least one drive means for automatically dispensing medicament or injection fluid to be dispensed, which drive means is usually provided in the form of a compression spring. The drive means is locked by the securing assembly 9 to prevent a release until the injection device 1 is deliberately activated by a user so that the drive assembly 8 is released and the injection device 1 thus activated. The first drive assembly is therefore held in its position relative to the base housing 2 by the securing assembly 9 until activated for the injection procedure.

It is possible for the base housing 2 to be of a split design. For example, the ampule 6, needle arrangement 7 and optionally also the needle guard element 10 together with the other drive unit may be arranged or disposed in the region of the distal end 3 of the injection device 1. The drive assembly 8 and the securing assembly 9 may be received or disposed in that part of the base housing 2 which incorporates or constitutes the proximal end 4. This being the case, that part of the injection device 1 in which the medicament or injection fluid is contained can be replaced with a new part containing a fresh medicament or fresh injection fluid on expiry of an expiry date. That part can be used again with the drive assembly 8 and securing assembly 9.

The essential part of the injection device 1 described here is the securing assembly 9 for cooperating with the drive assembly 8.

The securing assembly 9 sets the position of the at least one drive assembly 8 with respect to the base housing 2 until activated for the injection procedure. In the embodiment illustrated as an example here, the securing assembly 9 comprises a securing cap 12 and at least one retaining arm 13. In a known manner, the retaining arm 13 constitutes the connecting member to the drive assembly 8. The retaining arm(s) 13 is or are held in a latched position in the region of the proximal end 4, latched to a retaining disk and retained in a locked arrangement thereon by a securing pin 16 until activated. In a known manner, the securing pin 16 is disposed inside the at least one retaining arm 13, preferably at the axial center of the securing assembly 9, and prevents the retaining arm or arms 13 from moving radially inwards in the direction towards the longitudinal axis 11. Only when the securing cap 12 together with the securing pin 16 has been pulled back in the proximal direction and moved away from the contact region with the at least one retaining arm 13 can the at least one retaining arm 13 be moved out of its latched position to then enable the drive assembly 8 to be activated. In the embodiment illustrated as an example here, the base housing 2 in the region of its proximal end is configured, by means of a relative movement, to move the at least one retaining arm 13 out of its latched position in the radial direction into the space created by moving away the securing pin 16 and thus cause activation of the drive assembly 8.

The securing cap 12 in turn has a cap jacket 14 and a cap wall 15. The cap jacket 14 preferably extends continuously around the circumference and the cap wall 15 may also be referred to as an end wall or top wall. Disposed inside the cap jacket 14 on the cap wall 15, in particular at the center thereof, is the securing pin 16 extending in the direction of the longitudinal axis 11 and preferably also disposed at the center of the cap jacket 14. The securing pin 16 is preferably provided in the form of a bolt-type component, its axis or center axis being oriented along the longitudinal axis 11. The cap wall 15 is designed to secure the securing pin 16 at least in the region of its central portion continuously and completely.

In the storage position of the injection device 1, the securing cap 12 is disposed or retained on the base housing 2 in a securing position for the at least one drive assembly 8. Accordingly, in the securing position, the securing pin 16 positions the at least one retaining arm 13 of the securing assembly 9 in a stationary arrangement in a latched position in the radial direction relative to the longitudinal axis 11. This is a long-known arrangement and it is only when the securing pin 16 has been moved away from the region of the retaining arm or arms 13 that its latched position can be released by a corresponding activation operation and the drive assembly 8 can then be activated.

The securing cap 12 can be moved in the axial direction relative to the base housing 2 from its securing position into a releasing position in which the securing pin 16 is moved out of engagement with the retaining arm or arms 13.

In known securing mechanisms used to date for such injection devices 1, the securing cap is totally removed in order to release the drive assembly 8. This being the case, the orifice accommodating the securing pin 16 in the region of the proximal end 4 becomes visible, which can lead to incorrect operation. Given that an orifice can be seen both in the region of the distal end 3 and in the region of the proximal end 4 respectively, it was not clear to some users which of the two ends was the one to be placed on the respective body part for the injection procedure.

A separate guide arrangement 17 is provided or disposed between the securing cap 12 and the base housing 2. This being the case, an adjustment path 18 of the securing cap 12 in the axial direction can be defined between its securing position and releasing position relative to the base housing 2. The securing cap 12 is moved from a position lying closer to the distal end 3 in the direction of a position lying farther away. The direction is therefore selected so that the movement is effected towards the direction or end remote from the distal end 3. The selected and also usually standard direction of movement of the securing cap 12 may also be described as being in the proximal direction. Due to this limited adjustment path 18, the securing cap 12 is still retained or disposed on the base housing 2 even in its releasing position but the at least one retaining arm 13 for activating the drive assembly 8 is released by the securing pin 16. The releasing position of the securing cap 12 is indicated by dotted-dashed lines. Also schematically indicated are a first guide element 19 and at least one second guide element 20 cooperating therewith. The possible designs of these are described in more detail below.

As may be seen more clearly from FIGS. 2 and 3, the guide arrangement 17 may comprise at least one first guide element 19 and at least one second guide element 20 cooperating therewith. These two guide elements 19, 20 are used to define and restrict the limited adjustment path 18 in the axial direction between the securing cap 12 and the base housing 2. Depending on the design of the guide elements 19, 20, however, they may also be described as stops or projections which define the respective position, namely the releasing position and/or the securing position in terms of its position relative to the base housing 2. In this example of an embodiment, the at least one first guide element 19 is formed by a projection which is arranged or disposed on an internal face 21 of the cap jacket 14. Accordingly, the at least one projection constituting the first guide element 19 projects in the radial direction in the direction towards the longitudinal axis 11.

The at least one second guide element 20 may be formed by a guideway 22 provided in or on the base housing 2. For example, it is possible to arrange or dispose the guideway 22 in the external face of the base housing 2 and recessed therein. Furthermore, the guideway 22 may be disposed or arranged on the base housing in the region of the proximal end 4.

The longitudinal extension of the guideway 22 may be selected on the basis of various options. Based on the simplest and shortest displacement, the guideway 22 may extend exclusively in the axial direction for example, in which case there is no relative rotating movement of the securing cap 12 at all during the adjusting movement on the base housing. This is described and illustrated in more detail below with reference to FIG. 6.

However, another option would be for the guideway 22 to extend at an angle in its longitudinal extension relative to a plane oriented in the direction perpendicular to the longitudinal axis 11. In this case, the axial adjustment path 18 can also involve a rotating or pivoting movement of the securing cap 12 about the longitudinal axis 11 of the base housing 2. The pitch of the guideway 22 relative to the plane oriented in the direction perpendicular to the longitudinal axis 11 may be uniformly inclined from the securing position through to the releasing position for example.

However, another option, as may be seen in FIG. 3, is for the guideway 22 to have a different pitch with mutually different pitch angles in its longitudinal extension relative to the plane oriented in the direction perpendicular to the longitudinal axis 11. Accordingly, the pitch angle of the guideway 22 could be flatter in the region of the securing position and/or the releasing position than in the intermediate section extending between the securing position and releasing position. For example, in the region of the securing position and/or releasing position, the pitch angle of the guideway 22 extends parallel with the plane oriented in the direction perpendicular to the longitudinal axis 11.

It is also possible for the securing assembly 9 to further comprise a display unit 23. By means of the display unit 23, it is possible to indicate to the user at least one of the two positions of the securing cap 12 relative to the base housing 2. For example, the display unit 23 may comprise at least one first display means 24 which is provided or disposed in the region of the securing cap 12. In the simplest case, the first display means 24 might be provided in the form of a cap rim of the cap jacket 14 spaced at a distance apart from the cap wall 15. A second display means 25 of the display unit 23 may preferably be provided or disposed in the region of the base housing 2.

If the cap rim of the cap wall 15 is chosen as a first display means 24 for example, the second display means 25 may be provided in the form of a marking distributed or extending continuously around the circumference of the base housing 2 for example. This marking may be provided by means of a colored ring, a groove or similar, for example.

However, it would also be possible for the at least one first display means 24 to be formed by means of an orifice or a window in the cap jacket 14 and/or cap wall 15, as will be explained and illustrated below.

As may also be seen, the second display means 25 on the base housing 2 is provided by means of a marking ring, in particular a groove-shaped recess 26. Accordingly, after the axial displacement of the securing cap 12 about the adjustment path 18 extending in the axial direction, the second display means 25 appears underneath the cap rim of the cap jacket 14, as may be seen in FIG. 3 from the securing cap 12 indicated by dotted-dashed lines. The axial adjustment path 18 is travelled by means of a rotating or pivoting movement about a pivot angle by means of the cooperating first and second guide elements 19, 20.

FIG. 4 illustrates another embodiment of the injection device 1 which may be construed as an independent embodiment in its own right, in particular its securing assembly 9, the same reference numbers and component names being used to denote parts that are the same as those described in connection with FIGS. 1 to 3 above. To avoid unnecessary repetition, reference may be made to the more detailed description of FIGS. 1 to 3 above.

The embodiment of the securing assembly 9 illustrated in this instance is of a design similar to that described in detail above with reference to FIGS. 1 to 3. This being the case, only the design of the securing assembly 9 in the region of the proximal end 4 of the base housing 2 will be explained in detail.

Again, there is a securing cap 12 comprising the cap jacket 14, cap wall 15 and the securing pin 16 in the interior although the latter is not illustrated in detail. The design selected for the guide arrangement 17 is also the same as that in FIGS. 2 and 3. The first guide element or elements 19 is/are in turn disposed on the internal face 21 of the cap jacket 14 but are not illustrated in detail. The second guide element or elements 20 is/are provided respectively in the form of separate guideways 22, the longitudinal extension of which in turn defines the axial adjustment path 18, as already described above.

The display unit 23 in this instance is of a different design from the embodiment described above. Accordingly, the display unit 23 comprises an additional display mounting element 27 which is disposed or accommodated inside the cap jacket 14 and directly adjacent to the cap wall 15 and hence inside the securing cap 12 in the assembled state. The display mounting element 27 is also displaceable and guided on the base housing 2 in the axial direction in order to effect a movement or adjustment in the axial direction but is prevented from rotating or pivoting about the longitudinal axis 11.

The securing cap 12 is in turn pivotable or rotatable about the longitudinal axis 11 relative to the display mounting element 27. The extent of the pivot angle or turning angle of the securing cap 12 relative to the base housing 2 is defined or fixed by the guide arrangement 17, in particular the circumferential extension of the guideway 22. Furthermore, the display mounting element 27 is held in position on the securing cap 12 and relative thereto in the direction of the longitudinal axis 11. This can be achieved by means of retaining lugs or a groove-shaped recess provided in the internal face 21 of the cap jacket 14, although these are not illustrated. Accordingly, the display mounting element 27 is able to jointly effect the displacement along the axial adjustment path 18 together with the securing cap 12 but a relative pivoting movement or turning movement of the display mounting element 27 about the longitudinal axis 11 of the base housing 2 is prevented.

The display mounting element 27 based on this example of an embodiment comprises a disk-shaped main body 28 with an orifice 29 at its center. The orifice 29 is used to insert and accommodate the securing pin 16 disposed in the securing cap 12. The display mounting element 27 further comprises at least one guide web 30 extending or protruding out therefrom in the axial direction. The at least one guide web 30 may be disposed in the outer circumferential region of the disk-shaped main body 28. It is preferable to provide two such guide webs 30 to ensure a perfect axial guiding action of the display mounting element 27 on the base housing 2. The two guide webs 30 are disposed on the disk-shaped main body 28 in an arrangement diametrically opposite one another. In order to accommodate the guide web or webs 30, flat regions are provided on the base housing 2 in a complementary arrangement so that the two guide webs 30 can therefore also be received inside the securing cap 12.

In addition, a longitudinal guide arrangement 31 may be arranged or disposed between the at least one guide web 30 and the base housing 2. The longitudinal guide arrangement 31 may have cooperating and/or mutually engaging longitudinal guide elements, although these are not illustrated. They may be provided in the form of a groove-shaped recess and a lug or similar engaging therein.

Based on the embodiment illustrated as an example here, the display unit is formed by at least one first display means 24 configured as an orifice in the cap wall 15 of the securing cap 12. In this example of an embodiment, two orifices are provided, these two orifices being disposed diametrically opposite one another in the cap wall 15.

The display unit 23 in this instance further comprises the at least one second display means 25 arranged or disposed on the display mounting element 27, in particular on the disk-shaped main body 28. Accordingly, the second display means 25 is/are disposed on that side of the display mounting element 27 facing the cap wall 15 and the orifice or orifices provided therein.

The at least one second display means 25 may be selected and/or provided from the group comprising symbols, color coding, marking ring, image, groove-shaped recess, embossed print, braille.

The symbols or images could be selected as an open or closed lock, different color codes or similar for example. It is therefore unambiguously and clearly indicated to the user that when the securing cap is located in the securing position, the injection device 1 is still in its storage position and a release or activation of the drive assembly 8 is therefore not possible. It is not until after the securing cap 12 has been moved in the axial direction that it is indicated to the user by the second display means 25 becoming visible or appearing in the corresponding releasing position that the injection device 1 is ready for activation of the drive assembly 8 and the associated dispensing of medicament or injection fluid.

FIG. 5 illustrates another and optionally independent embodiment of the injection device 1 in its own right, in particular its securing assembly 9, the same reference numbers and component names being used to denote parts that are the same as those described with reference to FIGS. 1 to 4 above. To avoid unnecessary repetition, reference may be made to the more detailed description of FIGS. 1 to 4 given above.

In all the embodiments described and illustrated here, the securing cap 12 basically still continues to be disposed or retained on the base housing 2 in the releasing position as well, but the user nevertheless has the possibility of taking a cap-type part off the base housing 2 in order to release the injection device 1. To this end, the securing assembly 9 further comprises an overcap 32 which is detachably retained on the securing cap 12. The overcap 32 engages around the securing cap 12 in the region of its cap jacket 14 and in particular can completely accommodate the latter. Furthermore, mutually engaging catch means 33 may be provided between the overcap 32 and the securing cap 12, in particular in the region of the cap jacket 14 thereof.

For example, it would be possible to provide at least one catch projection 35 on a resilient arm 34 as catch means 33 on the securing cap 12. Other catch means 33 provided or disposed on the overcap 32, in particular its cap jacket, might be at least one catch recess 36 receiving the catch projection 35.

Since the at least one catch projection 35 is disposed on a resilient arm 34, it is possible for a user, having overcome the latching force, to move the overcap 32 out of engagement with the catch projection or projections 35 of the securing cap 12, thereby enabling the overcap 32 to be removed from the securing cap 12.

FIG. 6 illustrates two other and optionally independent embodiments of the injection device 1, in particular the securing assemblies 9 thereof, the same reference numbers and component names being used to denote parts that are the same as those described with reference to FIGS. 1 to 5 above. To avoid unnecessary repetition, reference may be made to the more detailed description of FIGS. 1 to 5 given above.

As briefly described above, yet other possible designs and arrangements of guide arrangements 17 for setting or defining the axial adjustment path 18 are illustrated.

Indicated by broken lines is the embodiment in which only an axial movement in a pure straight line is possible between the securing cap 12 and the base housing 2. The first guide element 19 is again disposed on the internal face 21 of the cap jacket 14. The longitudinal extension of the guideway 22 constituting the second guide element 20 is provided in the form of a groove-shaped recess but with only a purely axial extension on the base housing 2.

In the case of the embodiment indicated by solid lines, the first guide element or elements 19 in the form of individual projections are provided in the region of the open end of the cap jacket 14, in particular in the region of its cap rim. However, it would also be possible for the first guide element 19 to be provided in the form of a circumferentially extending collar or flange-type shoulder projecting in the direction towards the longitudinal axis 11.

The second guide element 20 is preferably provided on the base housing 2 in the form of two groove-shaped recesses. The axial spacing thus corresponds to the intended axial adjustment path 18. The securing cap 12 is therefore held in position in the region of the proximal end 4 of the base housing 2 both in the securing position of the securing cap 12 and in its releasing position. However, it would also be possible to provide only one of the two illustrated groove-shaped recesses as the second guide element 20.

Again with his example of an embodiment, the display unit 23 may be provided with at least one first display means 24 and at least one second display means 25. The design may be similar to that described above. Since there is preferably no circumferential relative movement between the base housing 2 and the securing cap 12 in this instance, the embodiment of the display unit 23 described with reference to FIG. 2 in particular may be selected.

If a guideway 22 is selected as the second guide element 20, it may also be designed so as to enable a movement out of the securing position by a pivoting or rotating movement in both the clockwise and counter-clockwise direction. If one of the two possible directions of rotation is selected and the securing cap 12 has been moved into the releasing position, the limited adjustment path 18 is travelled in the axial direction.

In addition to or independently of the above, it may also be in the case of all of the embodiments described above that there is an additional latching between the guide elements 19, 20 on reaching the releasing position. To this end, a projection or shoulder, not illustrated, could be provided in the guideway 22 and/or a recess for receiving the first guide elements 19.

Another variant should also be possible whereby the securing cap 12 can still be pulled from its releasing position back into the securing position before activating the drive assembly 8. This enables a user to return to the storage position of the injection device 1 again when the drive assembly 8 has not yet been activated.

The external cross-section of the cap jacket 14 may also be provided with flat regions and/or projections and/or may have a polygonal external cross-section to prevent the injection device 1 from rolling around.

The embodiments illustrated as examples represent possible variants and it should be pointed out at this stage that the invention is not specifically limited to the variants specifically illustrated, and instead the individual variants may be used in different combinations with one another and these possible variations lie within the reach of the person skilled in this technical field given the disclosed technical teaching.

The protective scope is defined by the claims. However, the description and drawings may be used to interpret the claims. Individual features or combinations of features from the different embodiments illustrated and described may be construed as independent inventive solutions or solutions proposed by the invention in their own right. The objective underlying the independent inventive solutions may be found in the description.

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10.

For the sake of good order, finally, it should be pointed out that, in order to provide a clearer understanding of the structure, some elements are illustrated to a certain extent out of scale and/or on an enlarged scale and/or on a reduced scale.

| List of reference numbers | |
|---|---|
| 1 | Injection device |
| 2 | Base housing |
| 3 | End |
| 4 | End |
| 5 | Support housing |
| 6 | Carpule |
| 7 | Needle arrangement |
| 8 | Drive assembly |
| 9 | Securing assembly |
| 10 | Needle guard element |
| 11 | Longitudinal axis |
| 12 | Securing cap |
| 13 | Retaining arm |
| 14 | Cap jacket |
| 15 | Cap wall |
| 16 | Securing pin |
| 17 | Guide arrangement |
| 18 | Adjustment path |
| 19 | First guide element |
| 20 | Second guide element |
| 21 | Internal face |
| 22 | Guideway |
| 23 | Display unit |
| 24 | First display means |
| 25 | Second display means |
| 26 | Recess |
| 27 | Display mounting element |
| 28 | Main body |
| 29 | Orifice |
| 30 | Guide web |
| 31 | Longitudinal guide arrangement |

-continued

| List of reference numbers | |
|---|---|
| 32 | Overcap |
| 33 | Catch means |
| 34 | Resilient arm |
| 35 | Catch projection |
| 36 | Catch recess |

The invention claimed is:

1. An injection, which injection device is designed to be displaceable from a storage position into an injection position, comprising
a sleeve-shaped base housing, which base housing has a distal end which can be directed towards a patient and a proximal end remote therefrom, between which ends a longitudinal axis extends,
an ampule containing an injection fluid to be dispensed during the injection procedure,
a needle arrangement disposed in front of the ampule in a direction of the distal end in the storage position of the injection device,
at least one drive assembly comprising a drive for automatically dispensing the injection fluid to be dispensed during the injection procedure,
a securing assembly, which securing assembly secures the at least one drive assembly in its position with respect to the base housing until activated for the injection procedure,
the securing assembly comprising a securing cap and at least one retaining arm, and the securing cap comprises a cap jacket, a cap wall and a securing pin which is disposed inside the cap jacket at a center on the cap wall and extending in the direction of the longitudinal axis, and
in the storage position on the external face of the base housing, the securing cap is retained in a securing position for the at least one drive assembly, and in the securing position, the securing pin is disposed inside the at least one retaining arm at the axial center of the securing assembly, and in the securing position, the securing pin holds the at least one retaining arm of the securing assembly in a stationary position in the radial direction relative to the longitudinal axis preventing a radial movement inwards in the direction towards the longitudinal axis, and the at least one retaining arm forms a connecting member to the drive assembly, and
a guide arrangement having at least one first guide element and at least one second guide element cooperating therewith is provided between the securing cap and the base housing, and
the ampule, the needle arrangement, the at least one drive assembly and the securing assembly are accommodated or disposed in the base housing, and the securing assembly and the drive assembly are disposed in that part of the base housing constituting the proximal end, and
the at least one first guide element is formed by a projection which is disposed or arranged on an internal face of the cap jacket and projects out from said internal face in the direction towards the longitudinal axis, and
the at least one second guide element is formed by a guideway which is arranged or disposed on the base housing proximate the securing cap and in that part of the base housing constituting the proximal end, or the at least one second guide element is formed by a groove-shaped recess and/or projection disposed or arranged proximate the securing cap and in that part of the base housing constituting the proximal end, and the securing cap is displaceable from its securing position in the axial direction and towards the end remote from the distal end into a releasing position, and the at least one first guide element and the at least one second guide element define an axial adjustment path of the securing cap delimited in the axial direction between its securing position and its releasing position, as a result of which the securing cap is still disposed and retained on the base housing in its releasing position and the at least one retaining arm for triggering and activating the drive assembly is also released by the securing pin at the same time, wherein the securing assembly further comprises an overcap which is detachably retained on the securing cap, wherein the securing assembly further comprises a display unit, which display unit displays at least one of the two positions of the securing cap relative to the base housing, and wherein the display unit further comprises a display mounting element, which display mounting element is disposed inside the cap jacket and directly adjacent to the cap wall, and the display mounting element is guided and displaceable on the base housing in the axial direction and the securing cap can also be pivoted relative to the display mounting element about the longitudinal axis, and the display mounting element is also held in position on the securing cap relative thereto in the direction of the longitudinal axis.

2. The injection device according to claim 1, wherein the guideway has a longitudinal extension, a first guideway region along the longitudinal extension, and a second guideway region along the longitudinal extension, wherein the first guideway region has a first pitch angle along the longitudinal extension relative to a plane oriented in a direction perpendicular to the longitudinal axis, and wherein the second guideway region has a second pitch angle along the longitudinal extension relative to the plane oriented in the direction perpendicular to the longitudinal axis, and wherein the first pitch angle is different than the second pitch angle.

3. The injection device according to claim 1, wherein the pitch angle of the guideway is flatter in the region of the securing position and/or the releasing position than in the intermediate section thereof extending between the securing position and the releasing position.

4. The injection device according to claim 1, wherein the display unit comprises at least one first display on the securing cap.

5. The injection device according to claim 4, wherein the at least one first display is formed by an orifice and/or a cap rim of the cap jacket spaced at a distance apart from the cap wall.

6. The injection device according to claim 1, wherein the display unit comprises at least one second display.

7. The injection device according to claim 1, wherein the display mounting element comprises a disk-shaped main body with an orifice disposed at its center and at least one guide web protruding in the axial direction therefrom.

8. The injection device according to claim 7, wherein the at least one guide web is disposed in the outer circumferential region of the disk-shaped main body.

9. The injection device according to claim 7, wherein a longitudinal guide arrangement is disposed or arranged between the at least one guide web and the base housing.

10. The injection device according to claim 1, wherein the display unit comprises at least one first display formed by an orifice in the cap wall of the securing cap.

11. The injection device according to claim 1, wherein the display unit comprises at least one second display disposed on the display mounting element.

12. The injection device according to claim 6 wherein the at least one second display is selected from the group consisting of a symbol, color coding, marking ring, groove-shaped recess, image, embossed print, and braille.

13. The injection device according to claim 1, wherein a mutually engaging catch is provided between the overcap and the securing cap.

14. The injection device according to claim 1, wherein the overcap engages around the securing cap.

15. The injection device according to claim 14, wherein the overcap completely accommodates the securing cap.

16. An injection device, which injection device is designed to be displaceable from a storage position into an injection position, comprising a sleeve-shaped base housing, which base housing has a distal end which can be directed towards a patient and a proximal end remote therefrom, between which ends a longitudinal axis extends, an ampule containing an injection fluid to be dispensed during the injection procedure, a needle arrangement disposed in front of the ampule in a direction of the distal end in the storage position of the injection device, at least one drive assembly comprising a drive for automatically dispensing the injection fluid to be dispensed during the injection procedure, a securing assembly, which securing assembly secures the at least one drive assembly in its position with respect to the base housing until activated for the injection procedure, the securing assembly comprising a securing cap and at least one retaining arm, and the securing cap comprising a cap jacket, a cap wall and a securing pin which is disposed inside the cap jacket at a center on the cap wall and extending in the direction of the longitudinal axis, and in the storage position on the external face of the base housing, the securing cap is retained in a securing position for the at least one drive assembly, and in the securing position, the securing pin is disposed inside the at least one retaining arm at the axial center of the securing assembly, and in the securing position, the securing pin holds the at least one retaining arm of the securing assembly in a stationary position in the radial direction relative to the longitudinal axis preventing a radial movement inwards in the direction towards the longitudinal axis, and the at least one retaining arm forms a connecting member to the drive assembly, and a guide arrangement having at least one first guide element and at least one second guide element cooperating therewith is provided between the securing cap and the base housing, and the ampule, the needle arrangement, the at least one drive assembly and the securing assembly are accommodated or disposed in the base housing, and the securing assembly and the drive assembly are disposed in that part of the base housing constituting the proximal end, and the at least one first guide element is formed by a projection which is disposed or arranged on an internal face of the cap jacket and projects out from said internal face in the direction towards the longitudinal axis, and the at least one second guide element is formed by a guideway which is arranged or disposed on the base housing proximate the securing cap and in that part of the base housing constituting the proximal end, or the at least one second guide element is formed by a groove-shaped recess and/or projection disposed or arranged proximate the securing cap and in that part of the base housing constituting the proximal end, and the securing cap is displaceable from its securing position in the axial direction and towards the end remote from the distal end into a releasing position, and the at least one first guide element and the at least one second guide element define an axial adjustment path of the securing cap delimited in the axial direction between its securing position and its releasing position, as a result of which the securing cap is still disposed and retained on the base housing in its releasing position and the at least one retaining arm for triggering and activating the drive assembly is also released by the securing pin at the same time, wherein the securing assembly further comprises an overcap which is detachably retained on the securing cap, wherein the securing assembly further comprises a display unit, which display unit displays at least one of the two positions of the securing cap relative to the base housing, wherein the display unit further comprises a display mounting element, which display mounting element is disposed inside the cap jacket and directly adjacent to the cap wall, and the display mounting element is guided and displaceable on the base housing in the axial direction and the securing cap can also be pivoted relative to the display mounting element about the longitudinal axis, and the display mounting element is also held in position on the securing cap relative thereto in the direction of the longitudinal axis, and wherein the display unit further comprises at least one first display formed by an orifice in the cap wall of the securing cap and at least one second display disposed on the display mounting element.

17. An injection device, which injection device is designed to be displaceable from a storage position into an injection position, comprising a sleeve-shaped base housing, which base housing has a distal end which can be directed towards a patient and a proximal end remote therefrom, between which ends a longitudinal axis extends, an ampule containing an injection fluid to be dispensed during the injection procedure, a needle arrangement disposed in front of the ampule in a direction of the distal end in the storage position of the injection device, at least one drive assembly comprising a drive for automatically dispensing the injection fluid to be dispensed during the injection procedure, a securing assembly, which securing assembly secures the at least one drive assembly in its position with respect to the base housing until activated for the injection procedure, the securing assembly comprising a securing cap and at least one retaining arm, and the securing cap comprising a cap jacket, a cap wall and a securing pin which is disposed inside the cap jacket at a center on the cap wall and extending in the direction of the longitudinal axis, and in the storage position on the external face of the base housing, the securing cap is retained in a securing position for the at least one drive assembly, and in the securing position, the securing pin is disposed inside the at least one retaining arm at the axial center of the securing assembly, and in the securing position, the securing pin holds the at least one retaining arm of the securing assembly in a stationary position in the radial direction relative to the longitudinal axis preventing a radial movement inwards in the direction towards the longitudinal axis, and the at least one retaining arm forms a connecting member to the drive assembly, and a guide arrangement having at least one first guide element and at least one second guide element cooperating therewith is provided between the securing cap and the base housing, and the ampule, the needle arrangement, the at least one drive assembly and the securing assembly are accommodated or disposed in the base housing, and the securing assembly and the drive assembly are disposed in that part of the base housing constituting the proximal end, and the at least one first guide element is formed by a projection which is disposed or arranged on an internal face of the cap jacket and projects out from said internal face in the direction towards the longitudinal axis, and the at least one second guide element is formed by a guideway which is arranged or disposed on the base housing proximate the securing cap and in that part of the base housing constituting the proximal end, or the at least one second guide element is formed by a groove-shaped recess and/or projection disposed or arranged proximate the securing cap and in that part of the base housing constituting the proximal end, and the securing cap is displaceable from its securing position in the axial direction and towards the end remote from the distal end into a releasing position, and the at least one first guide element and the at least one second guide element define an axial adjustment path of the securing cap delimited in the axial direction between its securing position and its releasing position, as a result of which the securing cap is still disposed and retained on the base housing in its releasing position and the at least one retaining arm for triggering and activating the drive assembly is also released by the securing pin at the same time, wherein the securing assembly further comprises an overcap which is detachably retained on the securing cap, and wherein the securing cap and the detachably retained overcap are displaceable together from the securing position to the releasing position.

18. The injection device according to claim 17, wherein the securing assembly further comprises a display unit, which display unit displays at least one of the two positions of the securing cap relative to the base housing.

19. The injection device according to claim 18, wherein the display unit comprises at least one first display formed by an orifice in the cap wall of the securing cap.

20. The injection device according to claim 18, wherein the display unit further comprises a display mounting element, which display mounting element is disposed inside the cap jacket and directly adjacent to the cap wall, and the display mounting element is guided and displaceable on the base housing in the axial direction and the securing cap can also be pivoted relative to the display mounting element about the longitudinal axis, and the display mounting element is also held in position on the securing cap relative thereto in the direction of the longitudinal axis.

21. The injection device according to claim 20, wherein the display mounting element comprises a disk-shaped main body with an orifice disposed at its center and at least one guide web protruding in the axial direction therefrom.

22. The injection device according to claim 21, wherein the at least one guide web is disposed in the outer circumferential region of the disk-shaped main body.

23. The injection device according to claim 21, wherein a longitudinal guide arrangement is disposed or arranged between the at least one guide web and the base housing.

24. The injection device according to claim 18, wherein the display unit comprises at least one first display on the securing cap.

25. The injection device according to claim 24, wherein the at least one first display is formed by an orifice and/or a cap rim of the cap jacket spaced at a distance apart from the cap wall.

26. The injection device according to claim 18 wherein the display unit comprises at least one second display.

27. The injection device according to claim 20, wherein the display unit comprises at least one second display disposed on the display mounting element.

28. The injection device according to claim 26 wherein the at least one second display is selected from the group consisting of a symbol, color coding, marking ring, groove-shaped recess, image, embossed print, and braille.

29. The injection device according to claim 17, wherein the guideway has a longitudinal extension, a first guideway region along the longitudinal extension, and a second guideway region along the longitudinal extension,
- wherein the first guideway region has a first pitch angle along the longitudinal extension relative to a plane oriented in a direction perpendicular to the longitudinal axis, and
- wherein the second guideway region has a second pitch angle along the longitudinal extension relative to the plane oriented in the direction perpendicular to the longitudinal axis, and
- wherein the first pitch angle is different than the second pitch angle.

30. The injection device according to claim 17, wherein the pitch angle of the guideway is flatter in the region of the securing position and/or the releasing position than in the intermediate section thereof extending between the securing position and the releasing position.

31. The injection device according to claim 17, wherein a mutually engaging catch is provided between the overcap and the securing cap.

32. The injection device according to claim 17, wherein the overcap engages around the securing cap.

33. The injection device according to claim 32, wherein the overcap completely accommodates the securing cap.

\* \* \* \* \*

UNITED STATES PATENT AND TRADEMARK OFFICE
CERTIFICATE OF CORRECTION

PATENT NO. : 10,744,263 B2
APPLICATION NO. : 15/762832
DATED : August 18, 2020
INVENTOR(S) : Markus Csenar et al.

Page 1 of 1

It is certified that error appears in the above-identified patent and that said Letters Patent is hereby corrected as shown below:

In the Claims

In Claim 1, Line 1 (Column 18, Line 12), "An injection" should read --An injection device--.

Signed and Sealed this
Sixth Day of October, 2020

Andrei Iancu
*Director of the United States Patent and Trademark Office*